(12) United States Patent
Suzuki

(10) Patent No.: US 6,531,643 B2
(45) Date of Patent: Mar. 11, 2003

(54) ABSORBENT ARTICLE WITH SILICONE COMPOUND LAYER

(75) Inventor: Sachiyo Suzuki, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/854,034

(22) Filed: May 10, 2001

(65) Prior Publication Data

US 2002/0002357 A1 Jan. 3, 2002

(30) Foreign Application Priority Data

May 19, 2000 (JP) ........................................ 2000-147826

(51) Int. Cl.⁷ ............................................... A61F 13/15
(52) U.S. Cl. ................................... 604/381; 604/385.01
(58) Field of Search ................................ 604/381–382, 604/385.01, 385.24–385.28

(56) References Cited

U.S. PATENT DOCUMENTS 5,292,316 A  3/1994 Suzuki ........................ 604/385
5,451,442 A  9/1995 Pieniak et al. ............... 428/218
5,599,417 A  2/1997 Glaug et al. ................. 156/227
6,025,535 A * 2/2000 Octavio et al. ............. 604/358
6,149,934 A * 11/2000 Krzysik et al. ............. 424/402

FOREIGN PATENT DOCUMENTS

EP    1 041 190 A2    4/2000
WO    WO 96/00548    11/1996

* cited by examiner

Primary Examiner—Dennis Ruhl
Assistant Examiner—C. Lynne Anderson
(74) Attorney, Agent, or Firm—Darby & Darby

(57) ABSTRACT

Disclosed is an absorbent article including a liquid-pervious top sheet to be in contact with the skin of a wearer, a back sheet, and an absorbent core sandwiched between the top sheet and the back sheet. A layer of silicone compound is formed on the surface of one of a side sheet provided on each side of the absorbent core, and a side portion of the back sheet extending outwardly from each side of the absorbent core.

12 Claims, 8 Drawing Sheets

ABSORBENT ARTICLE WITH SILICONE COMPOUND LAYER

BACKGROUND OF THE INVENTION

1. Field of the Invention

The present invention generally relates to an absorbent article. More precisely, it relates to an absorbent article having leak-preventing cuffs or flap portions for surely leading wearer's excretions to its top sheet and for preventing side leakage of the excretions through it. Further precisely, it relates to an absorbent article having such leak-preventing cuffs or flap portions coated with a silicone compound layer.

2. Description of the Related Art

Various absorbent articles for absorbing excretions are used, including, for example, sanitary napkins, pantiliners, disposable diapers, incontinence pads, etc. These absorbent articles comprise a liquid-pervious top sheet that is to be in contact with the skin of a wearer to pass the wearer's excretions through it, a back sheet that is to face the wearer's underwear, and an absorbent core sandwiched between the top sheet and the back sheet. On both sides, the absorbent articles have leak-preventing cuffs for preventing side leakage of excretions outside them. The absorbent articles of this type are made of vapor-pervious material to prevent them from being too much humidified. In these, for example, the leak-preventing cuffs are made of non-woven fabric of hydrophobic fibers.

In the absorbent articles of this type, however, excretions tend to adhere to the leak-preventing cuffs made of such non-woven fabric of hydrophobic fibers, and leak out of the leak-preventing cuffs owing to the wearer's body pressure from the wearer's weight and motion.

In addition, the excretions having adhered to the leak-preventing cuffs made of non-woven fabric of hydrophobic fibers often stain them, even though a little. In particular, menses and other fluid discharges containing protein firmly adhere to the leak-preventing cuffs made of such non-woven fabric, and stain them. Accordingly, if the leak-preventing cuffs of the sanitary napkins and the like are stained with menses, they will give an uncomfortable feeling to users when they are discarded after use.

On the other hand, high-viscosity fluid excretions such as loose feces and watery feces easily adhere to non-woven fabric. Therefore, with the disposable diapers and the like, loose feces and watery feces adhered to the leak-preventing cuffs made of non-woven fabric will give an uncomfortable feeling to users.

SUMMARY OF THE INVENTION

An object of the present invention is to provide an absorbent article which effectively prevents side leakage of excretions through it, and in which excretions hardly adhere to other region except for the top sheet.

According to an aspect of the invention, an absorbent article may comprise a liquid-pervious top sheet to be in contact with the skin of a wearer, a back sheet, and an absorbent core sandwiched between the top sheet and the back sheet, wherein;
a layer of silicone compound is formed on the surface of one of: a side sheet provided on each side of the absorbent core, and a side portion of the back sheet extending outwardly from each side of the absorbent core.

In the absorbent article of the invention, the silicone compound layer is formed on the leak-preventing cuffs and/or flap portions provided on both sides of the absorbent core. Being so constituted, therefore, the absorbent article prevents excretions from leaking out through the leak-preventing cuffs and/or flap portions. Additionally, excretions hardly adhere to the surface of the silicone compound layer, and even protein-containing menses hardly adhere thereto. Therefore, menses hardly adhere to the leak-preventing cuffs and the flap portions in the absorbent article to avoid giving an uncomfortable feeling to the users when the absorbent article is exchanged for a new one after used.

The absorbent article may have a leak-preventing cuff formed by the side sheet, and at least one surface of the leak-preventing cuff may be coated with the silicone compound layer.

The absorbent article may have a flap portion formed at least by the side sheet, and the surface of the flap portion to be in contact with the skin of a wearer may be coated with the silicone compound layer.

Preferably, the silicone compound layer has a two-layered structure comprising a first layer of a first silicone compound and a second layer of a second silicone compound formed on the first layer to be in contact with the skin of a wearer.

Also preferably, the silicone compound layer is formed of a mixture of a first silicone compound and a second silicone compound, and a larger amount of the second silicone compound than that of the first silicone compound appears on the surface of the silicone compound layer.

More preferably, the surface tension of the second silicone compound is lower than that of the first silicone compound.

Still more preferably, the surface tension of the second silicone compound is at most 30.0 mN/m.

Also preferably, the first silicone compound is a silicone resin.

Also preferably, the second silicone compound is a silicone oil. More preferably, the degree of polysiloxane skeleton introduction into the silicone oil falls between 30 and 100%, and the degree of polymerization of the silicone oil is at most 100.

DESCRIPTION OF THE PREFERRED EMBODIMENTS

Figure 1:
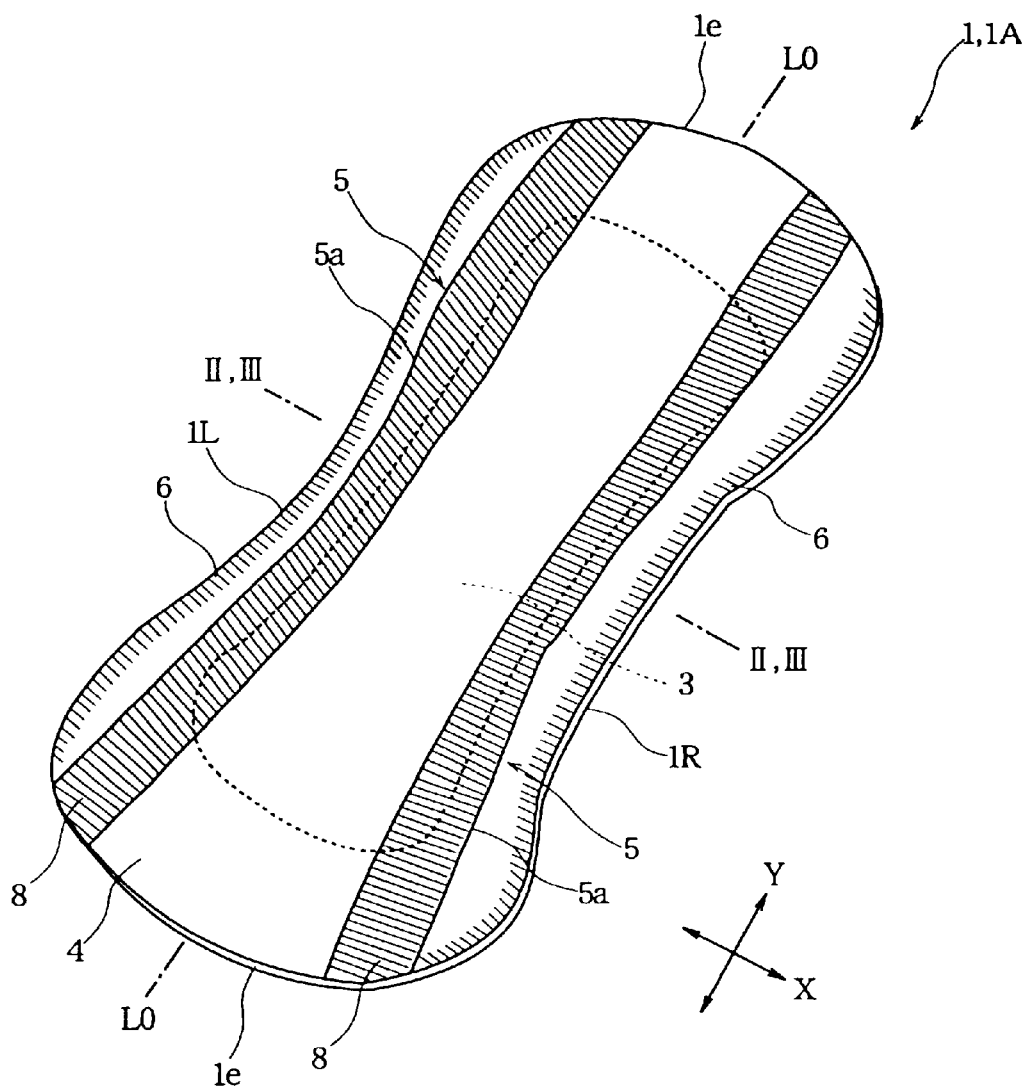
FIG. 1 is a plan view of a sanitary napkin of the first embodiment of the invention.
Figure 2:
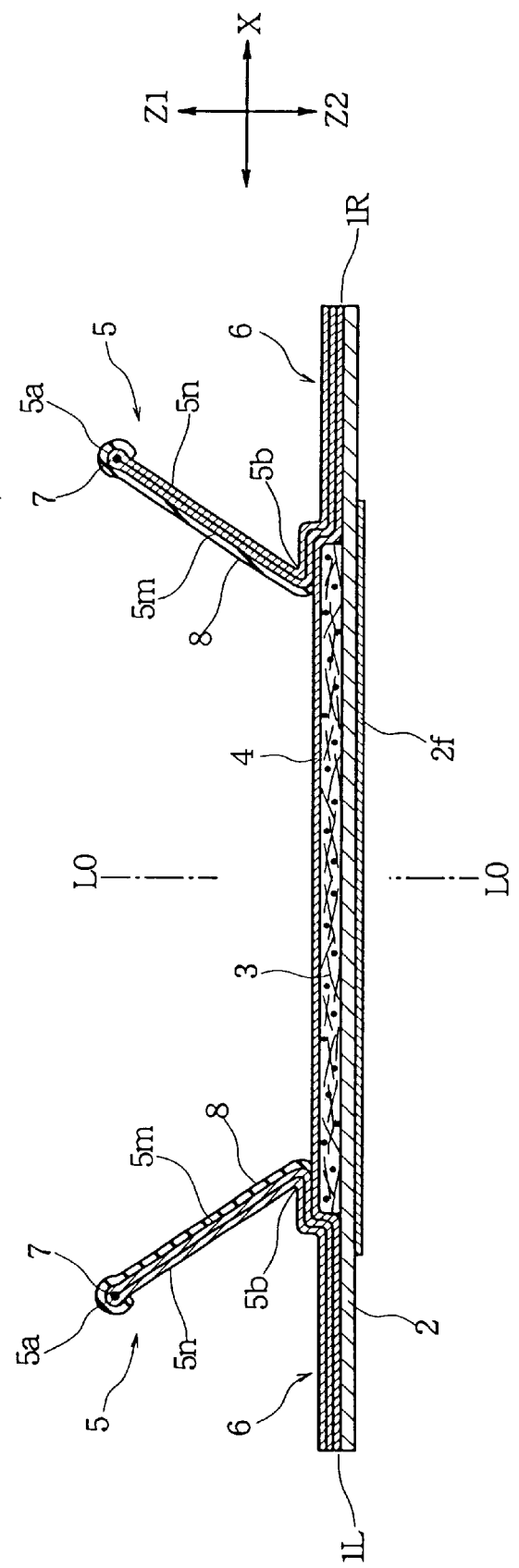
FIG. 2 is a cross-sectional view of FIG. 1, cut along the line II—II.

FIG. 1 is a plan view of a sanitary napkin of the first embodiment of the invention, and FIG. 2 is a cross-sectional view of FIG. 1, cut along the line II—II. In these drawings, the lateral direction of the sanitary napkin is designated by X, and the longitudinal direction thereof is designated by Y. The direction toward the skin of a wearer is designated by Z1; and the direction toward an external support such as wearer's underwear is designated by Z2.

As shown in FIG. 1 and FIG. 2, the sanitary napkin 1 comprises a liquid-pervious top sheet 4 to be in contact with the skin of a wearer, a back sheet 2 to face the wearer's underwear, and an absorbent core 3 sandwiched between the top sheet 4 and the back sheet 2. This is formed into an hourglass configuration. Precisely, around the hourglass-shaped absorbent core 3, the hourglass-shaped top sheet 4 and back sheet 2, both one size larger than the absorbent core 3, are bonded to each other. The thus-bonded parts of the top sheet 4 and the back sheet 2 extend outwardly from both sides of the absorbent core 3 to form flap portions 6, 6.

On both sides in the lateral direction of the sanitary napkin 1 (i.e., both side edge portions of the sanitary napkin 1), leak-preventing cuffs 5, 5 extend upwardly from the upper surface of the top sheet 4 disposed on the absorbent core 3, and these leak-preventing cuffs 5, 5 are extended in the longitudinal direction (Y direction) of the sanitary napkin 1.

Each leak-preventing cuff 5 is made of a sheet (this sheet is also referred to as a side sheet), and the sheet extends toward each side edge 1R, 1L in the lateral direction of the sanitary napkin 1, and is bonded to the upper surface of the top sheet 4. With that, the sheets forming the leak-preventing cuffs 5, 5 further form the flap portions 6, 6 along with the top sheet 4 and the back sheet 2.

The sheet is partly fixed to the top sheet 4 on the absorbent core 3 at a fixed end 5b, from which a free end 5a extends upwardly to form each leak-preventing cuff 5. An elastic member 7 which is stretched to extend in the direction Y, is fitted to the free end 5a.

On the body facing surface of the sanitary napkin 1, both ends of the leak-preventing cuffs 5, 5 in the longitudinal direction (direction Y) (i.e., both end edges thereof) are bonded to both longitudinal ends 1e, 1e of the sanitary napkin 1 (i.e., both end edges thereof) so that each free end 5a falls over the top sheet 4. As a result, the elastic member 7 is contracted under the condition where the external force is not applied to the sanitary napkin 1 (i.e., in a free condition), so that the sanitary napkin 1 is curved and deformed into a concave configuration (i.e., the center portion of the sanitary napkin 1 is downwardly protruded) in a side elevation of the sanitary napkin 1. Accordingly, the free end 5a of each leak-preventing cuff 5 extends upwardly in the direction Z1 from the fixed end 5b thereof, as shown in FIG. 2. In FIG. 2, the fixed end 5b is provided on the absorbent core 3, but it may be provided on the flap portion 6.

On an inner surface 5m of each leak-preventing cuff 5 that faces a longitudinal center line L0 of the absorbent article 1, a silicone compound layer 8 is formed from the fixed end 5b to the free end 5a. The silicone compound layer 8 has high water repellency. Accordingly, even when a large amount of the excretions such as menses not absorbed by the absorbent core 3 moves in the direction X, and further the body pressure of the user is applied to the contact portion of the layer 8 with the excretions, the excretions do not penetrate from the layer 8 to the outer surface 5n of the leak-preventing cuff 5. As a result, the cuff 5 can prevent side leakage of excretions. In addition, even when menses are contacted with the part coated with the silicone compound layer 8 they do not adhere to the surface of the silicone compound layer 8, but slip away from the surface of the layer 8 in the direction Z2 and are absorbed by the absorbent core 3. Therefore, when the used sanitary napkin 1 is discarded, the leak-preventing cuffs stained with menses will not be recognized by the user to avoid giving a visual uncomfortable feeling to the user.

If desired, the silicone compound layer 8 may be disposed on both the inner surface 5m and the outer surface 5n of the leak-preventing cuff 5. On the other hand, the silicone compound layer 8 completely covers the free end 5a of the leak-preventing cuff 5 in FIG. 2. However, as the case may be, the free end 5a may not be covered with the silicone compound layer 8.

The sheet to form the leak-preventing cuff 5 may be made of a non-woven fabric of fibers of at least one compound selected from the group consisting of cellulose compounds such as cupra, rayon, acetate, etc.; polyamide compounds such as nylon 6, nylon 66, aromatic nylons, etc.; polyvinyl alcohol compounds such as vinylon, etc.; polyvinylidene chloride compounds such as vinylidene, etc.; polyvinyl chloride compounds such as polyvinyl chloride, etc.; polyester compounds such as polyethylene terephthalate, polyacrylates, etc.; polyacrylonitrile compounds such as acryl, etc.; polyethylene compounds such as low-density polyethylene, high-density polyethylene, linear low-density polyethylene, etc.; polypropylene compounds such as polypropylene, etc.; polyurethane compounds such as polyurethane, etc.; polyalkylene-paraoxybenzoate compounds such as benzoates, etc., and/or natural fibers (of cotton, hemp, silk, pulp, etc.), or may also be made of a film or a net of at least one such compound. Preferably, the sheet is pervious to air. More preferably, it is made of a spun-laced non-woven fabric, spun-bonded non-woven fabric, air-through-bonded non-woven fabric or thermal-bonded non-woven fabric of polyethylene (PE) fibers, polypropylene (PP) fibers, polyethylene terephthalate (PET) fibers, or conjugated fibers (i.e., core/sheath fibers, side-by-side fibers) of PE/PP, PE/PET, etc. Also preferred are non-woven fabrics containing thermoplastic fibers, as they can be bonded to the sanitary napkin 1 by use of thermal welding to improve comfortable feeling to the skin of wearers.

Preferably, the surface of the sheet to form the leak-preventing cuff has a high degree of wettability in order that the leak-preventing cuff may be coated with a uniform and thin film of a silicone compound. For example, in cases where the leak-preventing cuff 5 is formed of a polyethylene film sheet or the like, it may be processed with corona discharge to increase the wettability thereof prior to being coated with a silicone compound.

To form the silicone compound layer 8, one or more of known silicone compounds such as silicone oil, silicone resin, silicone varnish, silicone rubber and others may be used either singly or as combined. When the layer 8 is formed of one type of a silicone compound, preferred for the silicone compound is silicone oil having a degree of polysiloxane skeleton introduction of from 30 to 100%. More preferably, the silicone oil has a degree of polymerization of at most 100.

The silicone compound layer 8 may be formed of two different types of silicone compounds (a two-layered structure of silicone compounds). Concretely, it is desirable that the layer 8 is composed of a first layer of a first silicone compound formed directly on the surface of the leak-preventing cuff 5, and a second layer of a second silicone compound formed on the top surface of the first layer. Alternatively, the silicone compound layer 8 is a layer of a mixture of a first silicone compound and a second silicone compound, and a larger amount of the second silicone compound than that of the first silicone compound appears on the surface of the layer 8. In these cases, it is preferable that the surface tension of the second silicone compound is lower than that of the first silicone compound. As a result, the excretions such as menses hardly adhere to the surface of the layer 8. The surface tension of silicone compounds referred to herein is meant to indicate the surface tension thereof in liquid or melted form. Even after being fixed (solidified), however, it is still desirable that the surface tension of the first silicone compound is higher than that of the second silicone compound.

The silicone compound layer 8 may be formed of two different types of silicone compounds, for example, according to any one of the following methods (1) to (3).

(1) The first silicone compound is applied to the surface of the sheet for forming the leak-preventing cuff 5, and then crosslinked to form an undercoat layer thereon; and after the undercoat layer has been fixed on the surface of the sheet, the second silicone compound is applied thereover to form a top layer.

(2) A mixture of a first silicone compound and a second silicone compound of which the surface tension is lower than that of the first silicone compound, is applied to the surface of the sheet for forming the leak-preventing cuff 5 to form a silicone mixture layer thereon; and after the second silicone compound has moved to the surface side of the silicone mixture layer and the first silicone compound has moved to the substrate sheet side, the respective silicone compounds are crosslinked.

(3) A mixture of a first silicone compound and a second silicone compound of which the surface tension is lower than that of the first silicone compound is applied to the surface of the sheet for forming the leak-preventing cuff 5 to form a silicone mixture layer thereon, and then this is crosslinked as it is, whereupon the mixture layer is subject to bleeding so that the second silicone compound moves to appear essentially on the surface of the resulting silicone compound layer 8.

In the method (1), the first silicone compound is applied to and fixed on the sheet, and then the second silicone compound is applied thereover to form a two-layered silicone compound layer. In this, therefore, the first and second silicone compounds may be any one of reactive polymers and non-reactive compounds.

In the methods (2) and (3), it is desirable that the first silicone compound is a reactive polymer and the second silicone compound is a non-reactive compound. In the method (2), when the mixture of the first and second silicone compounds is applied to the sheet and then left as it is for a while, the first silicone compound moves toward the substrate sheet side and the second silicone compound moves toward the surface side of the silicone compound layer. In this condition, the silicone compounds are crosslinked and the resulting silicone compound layer is fixed on the surface of the leak-preventing cuff 5.

In the method (3), immediately after the mixture of the first and second silicone compounds has been applied to the sheet, it is crosslinked under heat. With that, the second silicone compound moves toward the surface side of the resulting silicone compound layer by bleeding. This phenomenon will occur because the surface tension of the non-reactive second silicone compound is smaller than that of the first silicone compound. In case of the method (3), the amount of the second silicone compound gradually increases from the surface of the leak-preventing cuff 5 toward the surface of the layer 8.

Next, the first silicone compound will be described. Preferably, the surface tension of the first silicone compound is at most 30.0 mN/m. The surface tension referred to herein is measured in a standard condition (at an atmospheric temperature of 20° C.).

Preferably, the first silicone compound is a reactive silicone oil having a siloxane-structured basic skeleton. For example, it is desirable that the first silicone compound is at least one selected from the group consisting of methylhydrogensilicone oil, polydimethylsiloxane-diol, epoxy-modified silicone oil, carboxyl-modified silicone oil, methacryl-modified silicone oil, alcohol-modified silicone oil, mercapto-modified silicone oil, vinyl-modified silicone oil, and amino-modified silicone oil. By being dried under heat after coated, the silicone compound is firmly fixed on the surface of the leak-preventing cuff 5.

In the method (1), a non-reactive silicone compound may also be used for the first silicone compound. In this case, the non-reactive silicone compound is applied to the sheet of the leak-preventing cuff 5, and crosslinked through UV or EB exposure for radical polymerization so that the crosslinked compound is firmly fixed on the surface of the cuff 5, and thereafter a second silicone compound is applied thereover. For the non-reactive silicone compound, usable is a non-reactive silicone oil. Preferably, it is at least one compound selected from the group consisting of dimethylsilicone oil, methylphenylsilicone oil, alkyl-modified silicone oil, aralkyl-modified silicone oil, polyether-modified silicone oil, fluoroalkyl-modified silicone oil and fatty acid ester-modified silicone oil.

Apart from the above, the first silicone oil usable in the method (1) includes silicone varnishes such as polysiloxane, silicone-alkyd varnish, silicone-epoxy varnish, silicone-polyester vanish, silicone-acryl vanish, silicone-phenol varnish, silicone-urethane varnish, silicone-melamine varnish, etc.; silicone rubbers such as dimethylsilicone rubber, methylvinylsilicone rubber, methylphenylvinylsilicone rubber, methylfluoroalkylsilicone rubber, etc.

Next, the second silicone compound will be described. Preferably, the surface tension of the second silicone compound is lower than that of the first silicone compound. Concretely, it is desirable that the surface tension of the second silicone compound is lower by at least 5.0 mN/m than that of the first silicone compound. When the first silicone compound used for enhancing the ability of the layer 8 to prevent the adhesion of excretions thereto has a surface tension of at most 30.0 mN/m, it is desirable that the surface tension of the second silicone compound to be combined with the first silicone compound is at most 21.0 mN/m.

In the method (1), the second silicone compound is preferably a non-reactive silicone oil. For example, it is desirable that the second silicone compound is at least one selected from the group consisting of dimethylsilicone oil, methylphenylsilicone oil, methylhydrogensilicone oil, polydimethylsiloxane-diol, alkyl-modified silicone oil, aralkyl-modified silicone oil, polyether-modified silicone oil, fluoroalkyl-modified silicone oil, fatty acid ester-modified silicone oil, amino-modified silicone oil, epoxy-modified silicone oil, carboxyl-modified silicone oil, methacryl-modified silicone oil, alcohol-modified silicone oil, mercapto-modified silicone oil, and vinyl-modified silicone oil.

In case of the methods (2) and (3), the second silicone compound is preferably a non-reactive silicone compound. Concretely, it is desirable that the second silicone compound is at least one selected from the group consisting of polysiloxane, silicone-alkyd varnish, silicone-acryl varnish, silicone-phenol varnish, silicone-urethane varnish, silicone-melamine varnish, and dimethylsilicone rubber.

In the method (1), preferably, the thickness of the undercoat layer of the first silicone compound is at least 0.1 μm, more preferably at least 0.3 μm, for enhancing the ability of the layer 8 to prevent the adhesion of excretions thereto. Also preferably, the thickness of the top layer of the second silicone compound is at least 0.1 μm, more preferably at least 0.2 μm. In case of the methods (2) and (3), it is also desirable that the thickness of each separated layer falls within the range as above.

To fix the silicone compounds on the sheet, the silicone compounds may be crosslinked in any known manner. The mode of crosslinking the silicone compounds includes, for example, condensation crosslinking and addition crosslinking under heat; cationic polymerization and radical polymerization through UV exposure; and radical polymerization through EB exposure.

For applying the silicone compounds onto the sheet for the leak-preventing cuff 5, employable are any methods of using, for example, air doctor coaters, blade coaters, rod coaters, knife coaters, squeeze coaters, dip coaters, reverse roll coaters, transfer roll coaters, gravure coaters, kiss roll coaters, cast coaters, spray coaters, curtain coaters, calender coaters, extrusion coaters, etc. In the methods of coating the silicone compounds by use of such coaters, the kinematic viscosity of the silicone compounds is preferably at most 500 mm²/s in order that they can be spread uniformly on the surface of the sheet to form a thin and even layer thereon.

In the sanitary napkin 1, the liquid-pervious top sheet 4 is made of a non-woven fabric of PE fibers, PP fibers, PET fibers or their conjugated fibers all being treated to be hydrophilic, and the non-woven fabric may be any of spun-bonded non-woven fabrics, spun-laced non-woven fabrics, air-through-bonded non-woven fabrics, thermal-bonded non-woven fabrics, etc. As the case may be, the top sheet 4 may be a perforated resin sheet.

Preferably, the back sheet 2 is made of a liquid-impervious sheet. For example, the back sheet 2 is made of a vapor-pervious resin film; a spun-bonded non-woven fabric, a melt-blown non-woven fabric, or a composite non-woven fabric of two of them all being treated to be water repellent; or a laminate sheet of such a non-woven fabric and a vapor-pervious resin film. An adhesive layer 2f for fitting the sanitary napkin 1 to an external support such as underwear is disposed on the back surface of the back sheet 2 in the direction Z2. Preferably, the adhesive layer 2f is covered with a release sheet for protecting it until the sanitary napkin is used.

The absorbent core 3 is formed of powdery pulp or its mixture with super absorbent polymer, and the powdery pulp or its mixture with super absorbent polymer is wrapped with an absorbent sheet of tissue or the like.

The elastic member 7 is formed of an elastomer of, for example, natural rubber, synthetic rubber, polyurethane or styrene-butadiene copolymer, and it may be in any form of strings, filaments, films, strips (belts) and the like. For the elastic member 7, also usable are stretchable non-woven fabrics such as elastic spun-bonded non-woven fabrics, elastic melt-blown non-woven fabrics, etc. For this, the non-woven fabrics are cut into strips. In place of fitting the elastic member 7 to the free end 5a of the leak-preventing cuff 5, the cuff 5 itself may be made of a stretchable sheet or non-woven fabric, or may be made of an ordinary sheet or non-woven fabric corrugated to have a stretchability.

Figure 3:
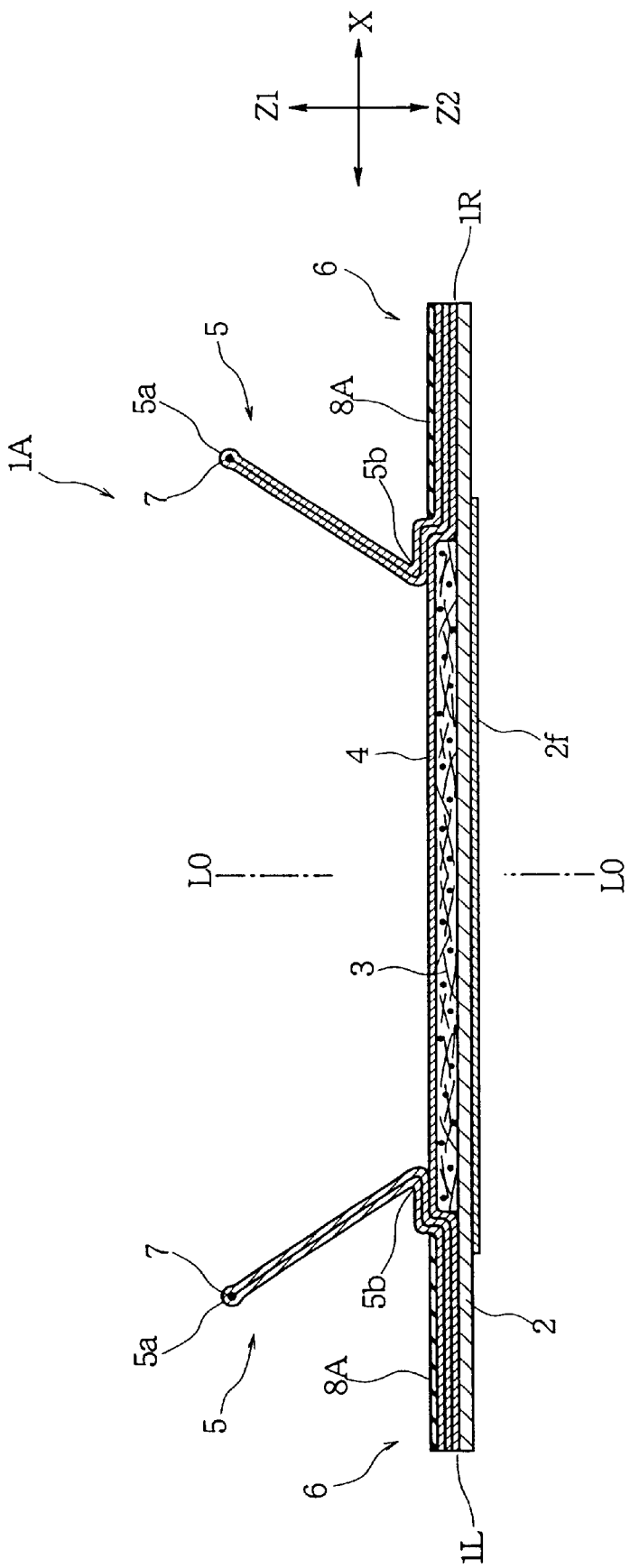
FIG. 3 is a cross-sectional view of a sanitary napkin of the second embodiment of the invention.

FIG. 3 is a cross-sectional view of a sanitary napkin of the second embodiment of the invention, and this corresponds to FIG. 2 showing the first embodiment set forth above. The sanitary napkin 1A of FIG. 3 differs from the sanitary napkin 1 of FIG. 2 in that the silicone compound layer 8 is not disposed on the surface of each leak-preventing cuff 5 but a silicone compound layer 8A is disposed on the surface of the flap portions 6, 6 that extend outwardly from both sides of the absorbent core 3 to both side edges 1R, 1L of the sanitary napkin 1A. In the sanitary napkin 1A of this embodiment, even when excretions such as menses flow from the center area of the top sheet 4 toward the flap portions 6, 6, the silicone compound layer 8A can prevent them from leaking outside the sanitary napkin 1A.

In this embodiment, the leak-preventing cuffs 5, 5 may be eliminated, and the flap portions 6, 6 coated with the layer 8A may be provided with elastic members extending in the direction Y at both side edges of the flap portions 6, 6 (that is, at both side edges 1R, 1L of the sanitary napkin 1A). Accordingly, the flap portions 6, 6 can rise toward the body facing side, thereby essentially serving as leak-preventing cuffs.

If desired, the silicone compound layer may be formed both on the leak-preventing cuffs 5, 5 and on the flap portions 6, 6.

Also if desired, the elastic member may be fitted both to the leak-preventing cuffs 5, 5 and to the flap portions 6, 6.

Figure 4:
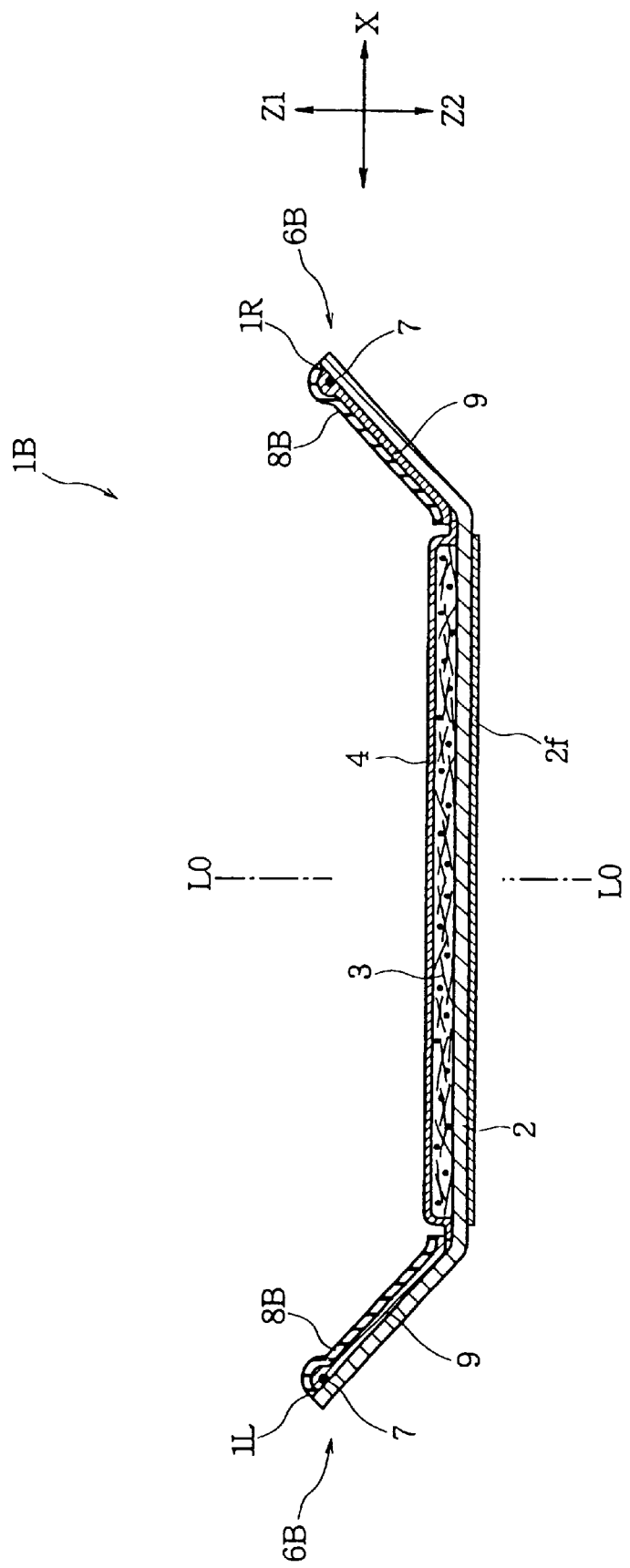
FIG. 4 is a cross-sectional view of a sanitary napkin of the third embodiment of the invention.

FIG. 4 is a cross-sectional view of a sanitary napkin of the third embodiment of the invention. On both side edge portions of a sanitary napkin 1B of FIG. 4, flap sheets 9, 9 are provided on the back sheet 2. The flap sheets 9,9 (this flap sheet is also referred to as a side sheet) extend from both side edges 1R, 1L of the sanitary napkin 1B to both side edges of the absorbent core 3 (precisely, in the vicinity of both side edges thereof) and are bonded to the back sheet 2 to form flap portions 6B, 6B. Being different from the sanitary napkins 1, 1A, the sanitary napkin 1B does not have leak-preventing cuffs 5, 5. In the sanitary napkin 1B, however, elastic members 7 are fitted to both side edges of the flap portions 6B, 6B (that is, to both side edges 1R, 1L of the sanitary napkin 1B), and each side edge of the flap portions 6B, 6B therefore rises toward the user's skin (in the direction Z1). On the surface of each flap sheet 9, disposed is a silicone compound layer 8B.

Figure 5:
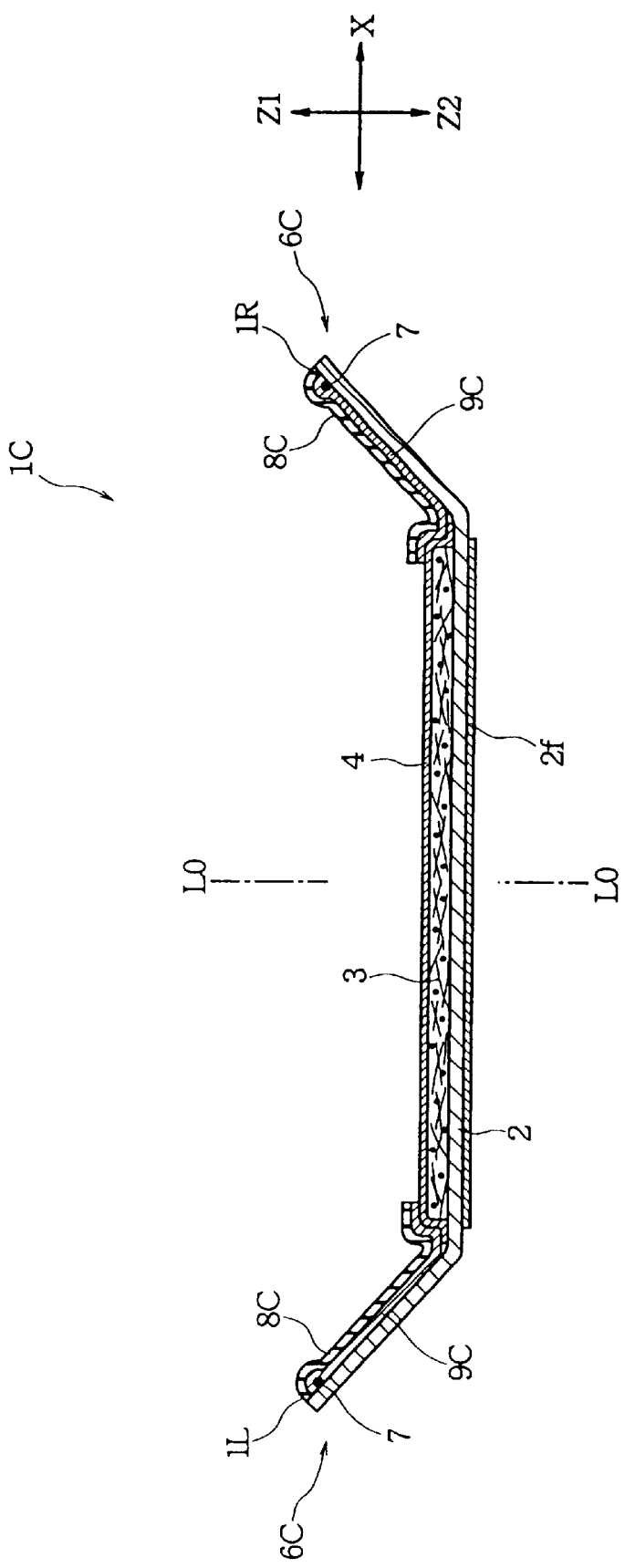
FIG. 5 is a cross-sectional view of a sanitary napkin of the fourth embodiment of the invention.

FIG. 5 is a cross-sectional view of a sanitary napkin of the fourth embodiment of the invention. The sanitary napkin 1C is an alternative embodiment of the sanitary napkin 1B of FIG. 4. In the sanitary napkin 1C of FIG. 5, the flap sheets 9C, 9C extend from both side edges 1R, 1L of the sanitary napkin 1C to the top sheet 4 under which the absorbent core 3 exists to overlap both side edges of the absorbent core 3. In this, silicone compound layers 8C, 8C also extend from both side edges 1R, 1L to the top sheet 4 under which the absorbent core 3 exists to overlap both side edges of the absorbent core 3 in order to cover the entire surface of the flap sheets 9C, 9C. In this alternative embodiment, the surface of the sanitary napkin 1C to be in contact with the user's skin (i.e., the body facing surface) is entirely covered with the silicone compound layer, except for the region under which the absorbent core 3 exists. Therefore, the ability of the sanitary napkin 1C to prevent leakage of excretions is further improved.

Figure 6:
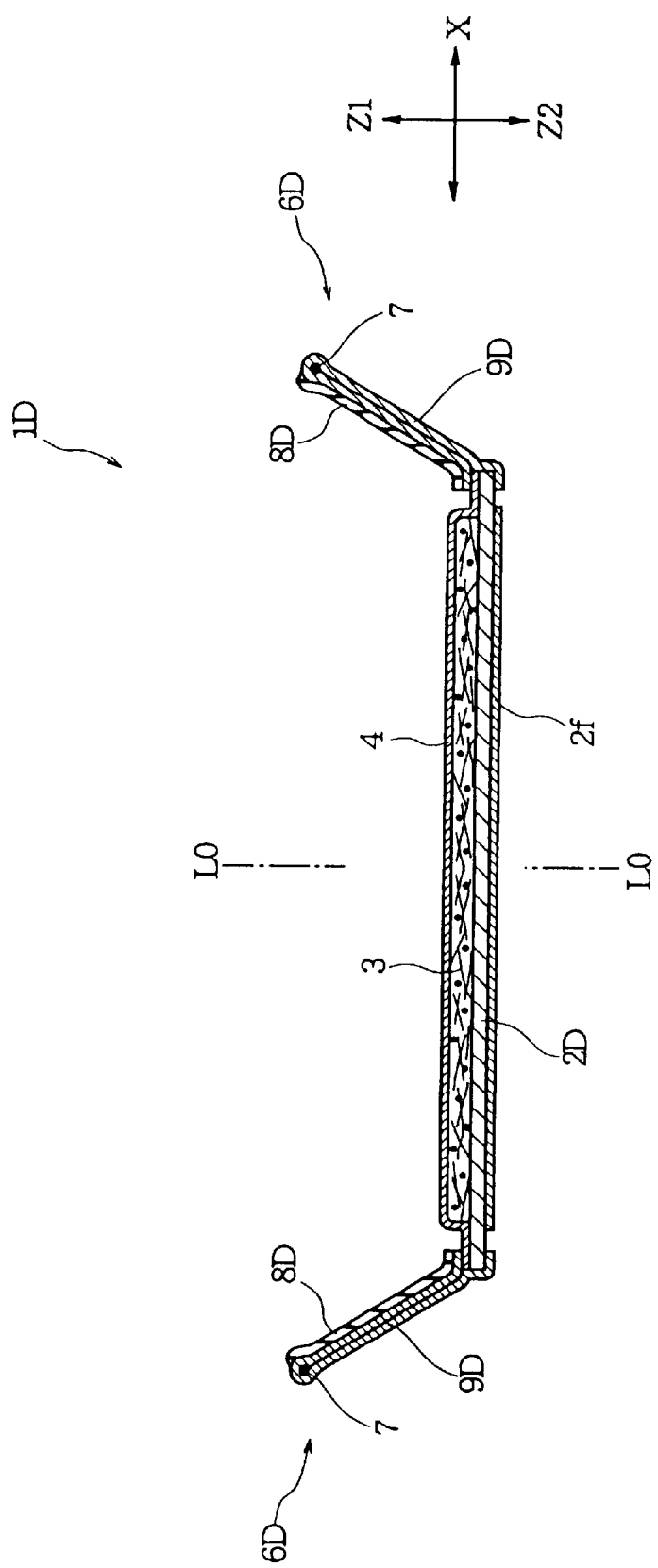
FIG. 6 is a cross-sectional view of a sanitary napkin of the fifth embodiment of the invention.
Figure 7:
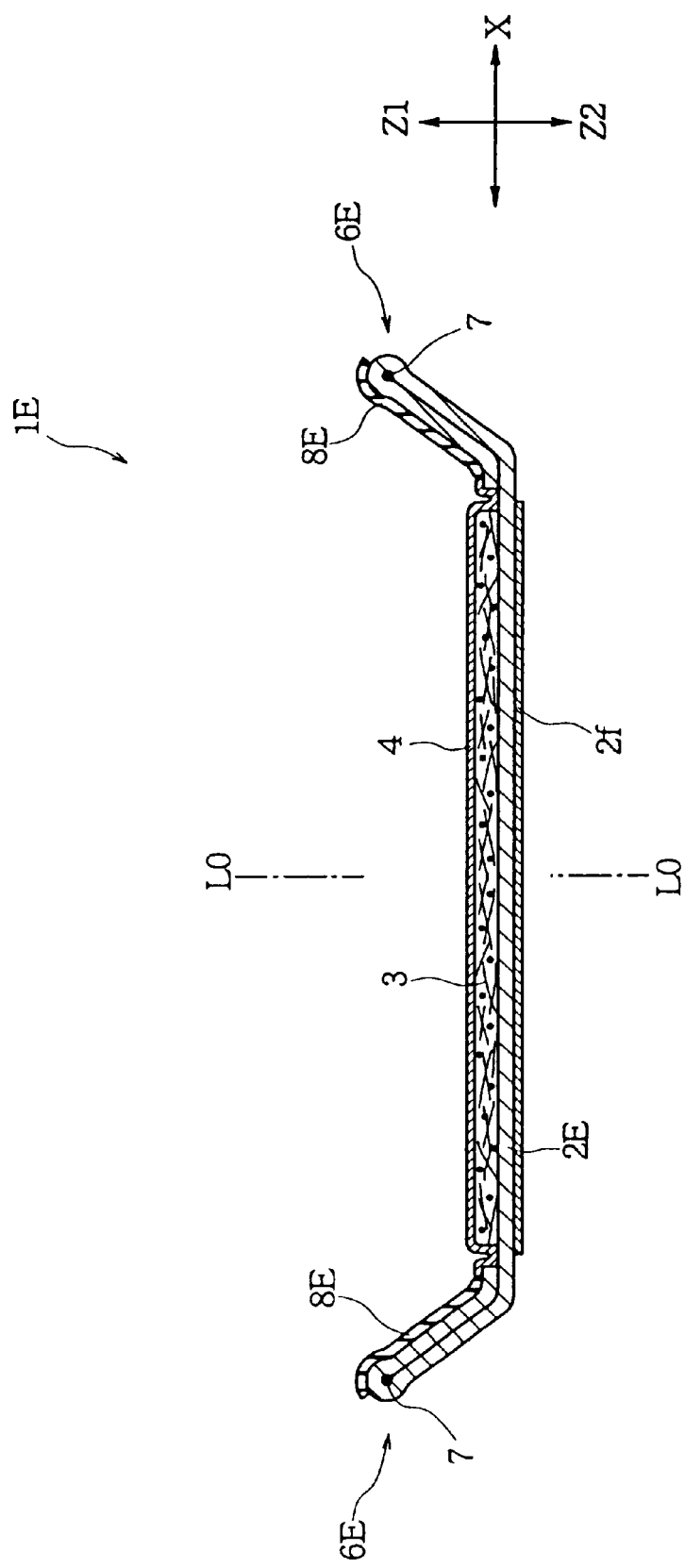
FIG. 7 is a cross-sectional view of a sanitary napkin of the sixth embodiment of the invention.

Any other various types of flap portions may apply to the sanitary napkins of the invention. For example, a flap portion 6D may be made of a flap sheet 9D only, and this may be coated with a silicone compound layer 8D, as shown in a sanitary napkin 1D of FIG. 6 which is the fifth embodiment of the invention. Alternatively, the back sheet 2E may be inwardly folded in the direction of the center line L0 at both side edges 1R, 1L of the sanitary napkin 1E to form flap portions 6E, 6E (i.e., this flap portion is formed by a side portion of the back sheet) as shown in a sanitary napkin 1E of FIG. 7 which is the sixth embodiment of the invention. In this embodiment, the inner surface of the back sheet 2E for forming each flap portion 6E is coated with a silicone compound layer 8E.

Figure 8:
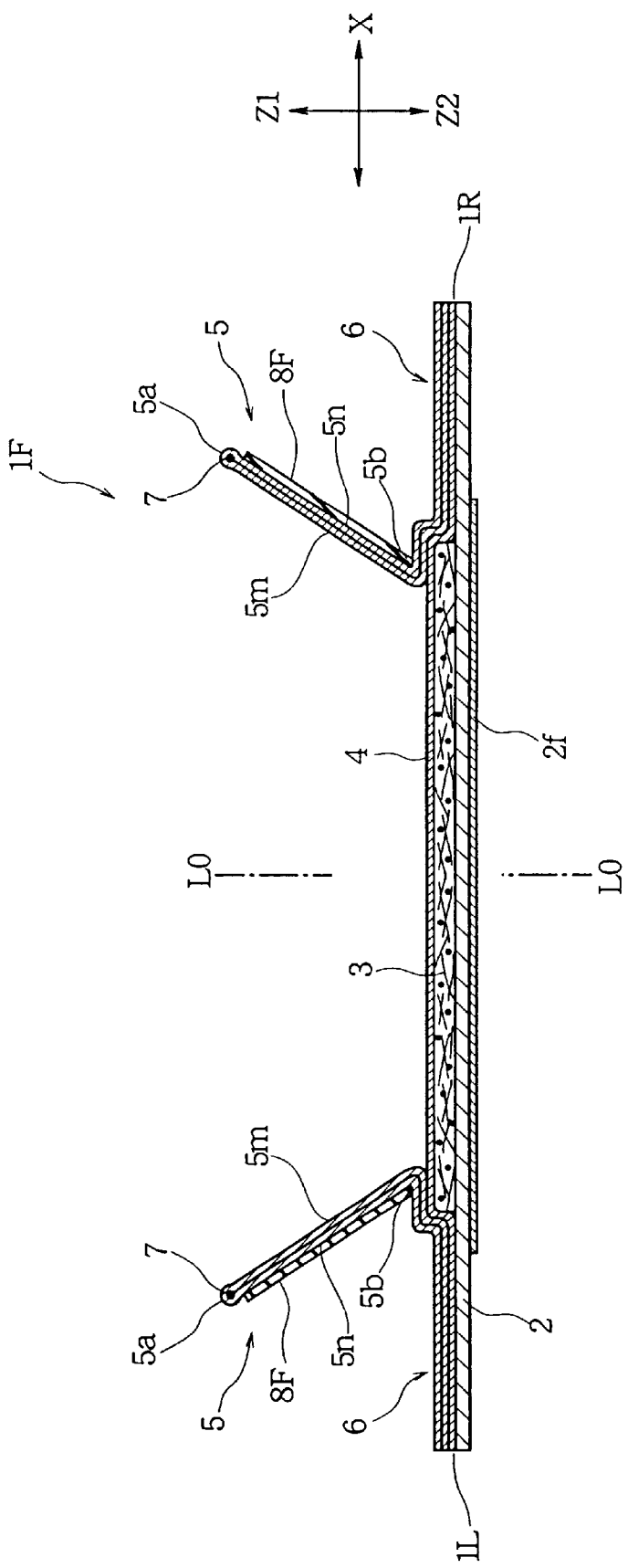
FIG. 8 is a cross-sectional view of a disposable diaper of the seventh embodiment of the invention.

FIG. 8 is a cross-sectional view of the seventh embodiment of the invention. The absorbent article shown in FIG. 8 is a disposable diaper 1F. In the disposable diaper 1F, the outer surface 5n of each leak-preventing cuff 5, facing outwardly in the direction X, is coated with a silicone compound layer 8F. As is the case with the embodiments set forth above, urine and feces do not leak outside through the silicone compound layer 8F formed on the outer surface 5n of each leak-preventing cuff 5.

The absorbent article of the invention is described hereinabove with reference to some examples of the sanitary napkin and the disposable diaper, but the invention is not limited to these examples. The invention may be applied to any other absorbent articles, including any other types of disposable diapers, incontinence pads, pantiliners and the like. Providing the silicone compound layer thereon is not limited to a pair of leak-preventing cuffs, but the layer may be provided on two pairs or three more pairs of leak-preventing cuffs.

EXAMPLES

The invention will be described in more detail with reference to the following Examples, which, however, are not intended to restrict the scope of the invention.

silicone resin layer of the sheet prepared in the same manner as in Example 1 to obtain the sheet of Example 3.

The sheets of Examples 1 to 3 were tested to measure the contact angle to a blood drop and to evaluate the slip-adhesion of blood, according to the test methods mentioned below. Comparative samples of polyethylene film and poly-tetrafluoroethylene film were also tested in the same manner. The tests are to confirm the ability of the samples to prevent the adhesion of excretions. The test data are given in Table 1.

Contact Angle

Equine blood is dropped onto the surface of the silicone compound layer of each sample. The contact angle in equilibrium is measured with a contact angle meter, "CA-S Micro-2 Model" manufactured by Kyowa Interface Science Co., Ltd.

Test for Slip-Adhesion of Blood

The surface of the silicone compound layer of each sample having a size of 30 mm×110 mm is rubbed 20 times with a cloth of spun-laced non-woven fabric. After having been thus rubbed, the sample is put on a horizontal table, and 0.2 g of equine blood is dropped thereon at 1 cm from its edge. With the sample thereon, the horizontal table is inclined at a rate of 1 degree/sec, and the angle of the horizontal table at the time when the blood has begun to flow down is measured. This angle is a slip angle. After the blood has flowed down completely, the amount of the blood having adhered to the sample is measured.

TABLE 1

|  |  |  |  | Before Rubbed | | After Rubbed 20 times | |
| --- | --- | --- | --- | --- | --- | --- | --- |
|  |  | Contact Angle (°) | Slip Angle (°) | Amount Adhered (g) | Condition of Adhesion | Amount Adhered (g) | Condition of Adhesion |
| Comp. Ex. 1 | polyethylene film | 89.8 | 30 | 0.035 | stripes | — | — |
| Comp. Ex. 2 | poly-tetrafluoroethylene film | 100.9 | 26 | 0.028 | stripes | — | — |
| Example 1 | silicone resin | 90.6 | 22 | 0.019 | dots | — | — |
| Example 2 | silicone oil | 86.8 | 3 | 0 | not adhered | 0.022 | discontinuous stripes |
| Example 3 | silicone resin + silicone oil | 87 | 3 | 0 | not adhered | 0 | not adhered |

Example 1

A UV-curable silicone diluted with a solvent was applied to the surface of a polyethylene film to form thereon a silicone layer having a thickness of 0.5 μm, then the solvent was dried up, and the thus-coated film was exposed to UV rays (350 nm, 120 W/cm) for 1 second. The sheet of Example 1 is obtained for forming leak-preventing cuffs.

Example 2

Dimethylsilicone oil (kinematic viscosity 20 mm$^2$/s; surface tension 20.8 mN/m) was applied to a polyethylene film to form thereon a silicone layer having a thickness of 20 μm, thereby obtaining the sheet of Example 2.

Example 3

The same dimethylsilicone oil as in Example 2 was applied in the same manner as in Example 2, over the From the test results as above, it is understood that blood flows down at a smaller angle of inclination on the silicone compound layer-coated sheets of the invention than on the comparative samples such as polyethylene film and fluorine-containing water-repellent film, so that the blood adhesion onto the sheets of the invention is smaller than that onto the comparative films. In addition, it is understood that the two-layered silicone compound layer is more resistant to friction than the single layered silicone compound layer. Accordingly, by applying the sheets of the invention to the leak-preventing cuffs and the flap portions of the sanitary napkin, it is possible to form superior leak-preventing cuffs and flap portions to which menstrual discharges or the like hardly adhere.

In the absorbent article of the invention, the leak-preventing cuffs and the flap portions are coated with a silicone compound layer, and excretions hardly pass through them. Therefore, the absorbent article of the invention effectively prevents leakage of excretions through it.

In addition, excretions hardly adhere to the surface of the silicone compound layer. In particular, even protein-containing menses and high-viscosity fluid excretions such as loose feces and watery feces hardly adhere to the surface thereof. After used, the adsorbent article of the invention does not give an uncomfortable feeling to users and caregivers when it is exchanged for a new one after used. In particular, when the silicone compound layer in the absorbent article has a two-layered structure or a substantially two-layered structure, it is resistant to friction and is hardly peeled off or broken under friction. In particular, the leak-preventing cuffs coated with such the two-layered silicone compound layer ensure higher water repellency and higher repellency to excretions.

While the invention has been described in detail and with reference to specific embodiments thereof, it will be apparent to one skilled in the art that various changes and modifications can be made therein without departing from the spirit and scope thereof.

What is claimed is:

1. An absorbent article-comprising a liquid-pervious top sheet for contact with skin of a wearer, a back sheet, and an absorbent core sandwiched between the liquid-pervious top sheet and the back sheet, wherein;

a layer of silicone compound is formed on a surface of one of: a side sheet provided on each side of the absorbent core, and a side portion of the back sheet extending outwardly from each side of the absorbent core;

wherein the layer of silicone compound has a two-layered structure comprising a first layer of a silicone resin and a second layer of a silicone oil formed on the first layer for contact with the skin of the wearer.

2. The absorbent article as set forth in claim 1, further comprising:

a leak-preventing cuff formed by the side sheet, and at least one surface of the leak-preventing cuff is coated with the silicone compound layer.

3. The absorbent article as set forth in claim 1, further comprising:

a flap portion formed at least by the side sheet, wherein a surface of the flap portion for contact with the skin of the wearer is coated with the silicone compound layer.

4. The absorbent article as set forth in claim 1, wherein a surface tension of the silicone oil is lower than that of the silicone resin.

5. The absorbent article as set forth in claim 1, wherein a surface tension of the silicon oil is at 30.0 mN/m.

6. The absorbent article as set forth in claim 1, wherein a degree of polysiloxane skeleton introduced into the silicone oil falls between 30 and 100%.

7. The absorbent article as set forth in claim 1, wherein a degree of polymerization of the silicone oil is at most 100.

8. The absorbent article as set forth in claim 1, wherein the silicone compound layer is formed of a mixture of a first silicone resin and a second silicone oil, and a larger amount of the second silicone oil than that of the first silicone resin appears on the surface of the silicone resin layer.

9. The absorbent article as set forth in claim 8, wherein a surface tension of the silicone oil is lower than that of the silicone resin.

10. The absorbent article as set forth in claim 8, wherein a surface tension of the silicone oil is at most 30.0 mN/m.

11. The absorbent article as set forth in claim 8, wherein a degree of polysiloxane skeleton introduced into the silicone oil is in a range of 30 and 100%.

12. The absorbent article as set forth in claim 8, wherein a degree of polymerization of the silicone oil is at most 100.

* * * * *